United States Patent [19]

Maender

[11] 4,207,216

[45] Jun. 10, 1980

[54] SCORCH INHIBITED VULCANIZABLE RUBBER COMPOSITIONS

[75] Inventor: Otto W. Maender, Copley, Ohio

[73] Assignee: Monsanto Company, St. Louis, Mo.

[21] Appl. No.: 948,118

[22] Filed: Oct. 2, 1978

[51] Int. Cl.² ............................................... C08F 8/34
[52] U.S. Cl. .......................................... 260/5; 260/42; 260/32; 260/42.44; 260/42.47; 260/45.8 SN; 260/763; 260/780; 525/348; 548/307
[58] Field of Search ................. 526/35; 260/45.8 SN, 260/5, 763, 780, 42.32, 42.44, 42.47; 525/348

[56] References Cited

U.S. PATENT DOCUMENTS

| | | | |
|---|---|---|---|
| 3,546,185 | 12/1970 | Coran et al. | 526/35 |
| 3,562,225 | 2/1971 | Coran et al. | 526/35 |
| 3,780,001 | 12/1973 | San | 526/35 |
| 3,847,879 | 11/1974 | Boustany et al. | 526/35 |
| 3,849,418 | 11/1974 | Boustany | 526/35 |
| 3,872,061 | 3/1975 | Boustany | 526/35 |
| 3,947,429 | 3/1976 | Sagawa et al. | 526/35 |

*Primary Examiner*—William F. Hamrock
*Attorney, Agent, or Firm*—Larry R. Swaney

[57] ABSTRACT

Vulcanizable rubber compositions inhibited from premature vulcanization by incorporation of hindered alkylthioimidazolidinetriones are described.

15 Claims, No Drawings

SCORCH INHIBITED VULCANIZABLE RUBBER COMPOSITIONS

This invention relates to improved vulcanizable rubber compositions inhibited from premature vulcanization, to an improved process for inhibiting premature vulcanization of rubber, and to compounds which are especially potent premature vulcanization inhibitors.

BACKGROUND OF THE INVENTION

The inhibition of premature vulcanization of vulcanizable rubber composition by using N-(thio)amides including hindered-alkylthio amides is known, for example, U.S. Pat. Nos. 3,546,185, 3,686,169, 3,780,001, 3,737,438, 3,849,418, 3,872,061 and British Pat. No. 1,345,144. 1,3-Di(1-chloro-1-nitropropylthio)imidazolidinetrione, (parabanic acid), is a known fungicide, U.S. Pat. No. 3,468,905.

SUMMARY OF THE INVENTION

It has been discovered that hindered-alkylthio derivatives of imidazolidinetrione are especially potent premature vulcanization inhibitors. Surprisingly, the presence of two hydrocarbon substituents on the alpha carbon of the alkyl radical enhances prevulcanization inhibitor activity. The improved inhibitors of the invention are characterized by the formula

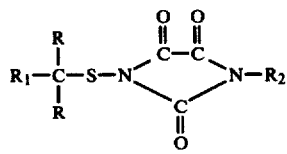

in which each R independently is alkyl of 1-5 carbon atoms, $R_1$ is alkyl of 1-12 carbon atoms, $R_2$ is hydrogen, alkyl of 1-12 carbon atoms, aryl of 6-10 carbon atoms, aralkyl of 7-10 carbon atoms or

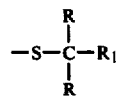

Examples of satisfactory radicals for R and $R_1$ are methyl, ethyl, propyl, isopropyl, n-butyl, sec-butyl, t-butyl, isobutyl, pentyl, hexyl, heptyl, octyl, t-octyl (1,1,3,3-tetramethylbutyl), nonyl, decyl and dodecyl. Examples of satisfactory radicals for $R_2$ are alkyl radicals as illustrated above for $R_1$ and phenyl, o-tolyl, m-tolyl, p-tolyl, 2,4-dimethylphenyl, 4-t-butyl-phenyl, naphthyl, benzyl, α-methylbenzyl, α,α-dimethylbenzyl, phenethyl, 3-phenylpropyl and 4-phenylbutyl. In preferred compounds, R is straight-chain alkyl, preferably, methyl and $R_1$ is $C_1$-$C_5$ alkyl. In another preferred class of compounds, $R_2$ is

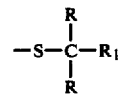

Inhibitors of the invention are prepared by reacting the appropriate sulfenyl chloride with imidazolidinetrione or N-substituted imidazolidinetrione, in the presence of a hydrogen chloride acceptor. Alternatively, sulfenyl chloride is reacted with a mono- or di-alkali metal salt of the aforesaid intermediates.

Illustrative examples of compounds of the invention are:
1,3-di(t-butylthio)imidazolidinetrione
1,3-di(1,1-dimethylpropylthio)imidazolidinetrione
1,3-di(1,1,3,3-tetramethylbutylthio)imidazolidinetrione
1,3-di(1,1-dimethylbutylthio)imidazolidinetrione
1,3-di(1-ethyl-1-methylpropylthio)imidazolidinetrione
1,3-di(1,1,2,2-tetramethylpropylthio)imidazolidinetrione
1,3-di(1,1-dimethylheptylthio)imidazolidinetrione
1,3-di(1,1-dimethylpentylthio)imidazolidinetrione
1,3-di(1,1-dimethylhexylthio)imidazolidinetrione
1,3-di(1,1-diethylpropylthio)imidazolidinetrione
1-(t-butylthio)-3-phenyl-imidazolidinetrione
1-(t-butylthio)-3-benzyl-imidazolidinetrione
1-(t-butylthio)-3-methyl-imidazolidinetrione
1-(t-butylthio)-3-ethyl-imidazolidinetrione
1-(t-butylthio)-3-propyl-imidazolidinetrione
1-(t-butylthio)-3-isopropyl-imidazolidinetrione
1-(t-butylthio)-3-n-butyl-imidazolidinetrione
1-(t-butylthio)-3-t-butyl-imidazolidinetrione
1-(t-butylthio)-3-(1-methylphenyl)imidazolidinetrione
1-(t-butylthio)-3-(4-methylphenyl)imidazolidinetrione
1-(t-butylthio)-3-(2-phenethyl)imidazolidinetrione
1-(t-butylthio)-3-(naphthyl)imidazolidinetrione
1-(t-butylthio)-3-(n-hexyl)imidazolidinetrione
1-(t-butylthio)-3-(n-octyl)imidazolidinetrione
1-(t-butylthio)-3-(n-decyl)imidazolidinetrione and
1-(t-butylthio)-3-(n-dodecyl)imidazolidinetrione Illustrative examples of compounds of the invention when $R_2$ is hydrogen are:
1-(t-butylthio)imidazolidinetrione
1-(1,1-dimethylpropylthio)imidazolidinetrione
1-(1,1,3,3-tetramethylbutylthio)imidazolidinetrione
1-(1,1-dimethylbutylthio)imidazolidinetrione
1-(1-ethyl-1-methylpropylthio)imidazolidinetrione
1-(1,1,2,2-tetramethylpropylthio)imidazolidinetrione
1-(1,1-dimethylheptylthio)imidazolidinetrione
1-(1,1-dimethylpentylthio)imidazolidinetrione
1-(1,1-dimethylhexylthio)imidazolidinetrione and
1-(1,1-diethylpropylthio)imidazolidinetrione The inhibitors of the invention are incorporated into rubber stocks by mixing on a mill or in an internal mixer such as a Banbury mixer. However, the inhibitors may be incorporated by addition to latex, if desired. The process of the invention is particularly applicable to sulfur-vulcanizable rubber compositions which rubber compositions contain a sulfur vulcanizing agent such as an amine disulfide or a polymeric polysulfide but preferably, the vulcanizing agent is elemental sulfur. Rubber compositions containing organic accelerating agents are particularly improved by the inhibitors of the invention. Any organic accelerating agents in an amount effective to accelerate the sulfur vulcanization of rubber is satisfactory in the practice of this invention. Effective amounts generally are within the range of 0.1 to 5.0 parts per 100 parts by weight rubber. Examples of suitable accelerators are described in U.S. Pat. No. 3,546,185, col. 9, lines 53–75 and in U.S. Pat. No. 3,780,001, col. 4, lines 43–72. The process of the invention is applicable to a wide variety of natural and synthetic rubbers and mixtures thereof and especially applicable to diene rubbers. Examples of satisfactory rubbers are described in U.S. Pat. No. 3,546,185, col. 10, lines 15-21 and U.S. Pat. No. 3,780,001, col. 5, lines 5-33. The vulcanizable composition may also contain conventional compounding ingredients such as reinforcing pigments, extenders, processing oils, antidegradants and the like.

Small amounts of inhibitors are effective to inhibit premature vulcanization. Improvements in processing safety may be observed with 0.05 parts or less of inhibitor per 100 parts rubber. Although there is no upper limit in the amount of inhibitor used, generally the amount does not exceed 5 parts inhibitor per 100 parts rubber. Typically, the amount of inhibitor added is about 0.1 to 2.5 parts per 100 parts rubber with amounts of about 0.2 to 1 part inhibitor per 100 parts rubber being commonly used. Methods for determining scorch times and curing characteristics of rubber stocks used in demonstrating this invention are described in U.S. Pat. No. 3,546,185, col. 13, lines 30-53. Vulcanizates are prepared by heating vulcanizable compositions for the times indicated from rheometer data to obtain optimum cure.

DESCRIPTION OF PREFERRED EMBODIMENTS

Example 1

A 164.5 g solution of 1,1-dimethylethane sulfenyl chloride (0.3 mole) in hexane is added slowly over about one hour with stirring at 18°-31° C. to a slurry of 22.1 g (0.14 mole) disodium imidazolidinetrione in 100 ml of hexane. The reaction mass is stirred for an additional 0.5 hours then filtered. The filter cake is washed twice with hexane, slurried in water and filtered again. The filter cake is washed with water, washed twice with hexane, then is allowed to air dry. 29.8 Grams of 1,3-di(t-butylthio)imidazolidinetrione, m.p. 113°-4° C., is recovered. Recrystallized from hexane the product melts at 114°-5° C. Identification is confirmed by infra red analysis, NMR spectral analysis and by liquid chromotography. Chemical analysis gives 20.7% sulfur compared to 22.1%S calculated for $C_{11}H_{18}N_2O_3S_2$.

Example 2

A 59 g. solution of 1,1-dimethylethane sulfenyl chloride (0.1 mole) in hexane is added slowly over a 20 minute period with stirring at 22°-30° C. to a slurry of 21.2 g. (0.1 mole) 1-phenyl-3-sodium imidazolidinetrione in 150 ml of hexane. After stirring about 45 additional minutes, the reaction mass is filtered. The filter cake is washed with water, dissolved in hot toluene and filtered. The filtrate is concentrated and slurried in hexane to give a white solid. 1-Phenyl-3-(t-butylthio)imidazolidinetrione, m.p. 171°-3° C., recrystallized from heptane, is obtained. Identification is confirmed by NMR spectral analysis and by liquid chromotography. Chemical analysis gives 11.1% sulfur compound to 11.5%S calculated for $C_{13}H_{14}N_2O_3S$.

Example 3

The procedure of Example 1 is followed except 1,1,3,3 tetramethylbutane sulfenyl chloride is substituted for 1,1-dimethylethane sulfenyl chloride. The reaction mass is washed in water and the solvent is evaporated to yield 1,3-di(t-octylthio)imidazolidinetrione, a yellow oil. NMR spectral analysis indicates the presence of some disulfide by-product.

Example 4

The procedure of Example 2 is repeated except 1-ethyl-3-sodium imidazolidinetrione is substituted in place of 1-phenyl-3-sodium imidazolidinetrione. 1-Ethyl-3-(t-butylthio)-imidazolidinetrione, m.p. 100.5°-102° C. recrystallized from hexane, is recovered. Chemical analysis gives 13.2% sulfur compared to 13.9%S calculated for $C_9H_{14}N_2O_3S_2$.

1-(t-Butylthio)imidazolidinetrione is prepared by adding a solution of 1,1-dimethylethane sulfenyl chloride (0.1 mole) to a stirred slurry of sodium imidazolidinetrione (0.1 mole). 1-(t-Butylthio)imidazolidinetrione, m.p. 150.5°-152° C. recrystallized from toluene, is recovered.

The process of the invention is demonstrated by incorporating inhibitors into portions of rubber stocks comprising the ingredients shown in the Tables. All parts are by weight.

Table 1

| Stocks | 1 | 2 | 3 | 4 |
|---|---|---|---|---|
| Natural rubber | 100 | 100 | 100 | 100 |
| Carbon black | 40 | 40 | 40 | 40 |
| Processing oil | 10 | 10 | 10 | 10 |
| Hydrocarbon wax | 2 | 2 | 2 | 2 |
| Zinc oxide | 5 | 5 | 5 | 5 |
| Stearic acid | 1 | 1 | 1 | 1 |
| Sulfur | 2.5 | 2.5 | 2.5 | 2.5 |
| N-(t-butyl)-2-benzothiazole sulfenamide | 0.6 | 0.6 | 0.6 | 0.6 |
| 1,3-di-(t-butylthio) imidazolidinetrione | — | 0.4 | — | — |
| 1,3-di-(t-octylthio) imidazolidinetrione | — | — | 0.4 | — |
| 1-phenyl-3-(t-butylthio) imidazolidinetrione | — | — | — | 0.4 |
| Mooney Scorch @ 135° C. | | | | |
| $t_5$, minutes | 11.7 | 22.1 | 17.8 | 19.6 |
| % increase in scorch delay | — | 89 | 52 | 68 |
| Stress-Strain @ 153° C. | | | | |
| $M_{300}$, MPa | 7.6 | 7.1 | 7.7 | 7.4 |
| UTS, MPa | 25.0 | 25.4 | 25.0 | 23.2 |
| Elong., % | 610 | 650 | 620 | 590 |

Table 2

| Stocks | 1 | 2 | 3 | 4 | 5 |
|---|---|---|---|---|---|
| Natural rubber | 100 | 100 | 100 | 100 | 100 |
| Carbon black | 40 | 40 | 40 | 40 | 40 |
| Processing oil | 10 | 10 | 10 | 10 | 10 |
| Hydrocarbon wax | 2 | 2 | 2 | 2 | 2 |
| Zinc oxide | 5 | 5 | 5 | 5 | 5 |
| Stearic acid | 1 | 1 | 1 | 1 | 1 |
| Sulfur | 2.5 | 2.5 | 2.5 | 2.5 | 2.5 |
| N-(t-butyl)-2-benzothiazole sulfenamide | 0.6 | 0.6 | 0.6 | 0.6 | 0.6 |
| 1,3-di(trichloromethylthio) imidazolidinetrione | — | 0.4 | — | — | — |
| 1-ethyl-3-(t-butylthio) imidazolidinetrione | — | — | 0.4 | — | — |
| 1-(t-butylthio)imidazolidinetrione | — | — | — | — | 0.4 |
| Mooney Scorch @ 135° C. | | | | | |
| $t_5$, minutes | 10.7 | 11.6 | 21.5 | 11.5 | 18.8 |
| % increase in scorch delay | — | 88% | 101% | — | 63% |
| Stress-Strain @ 153° C. | | | | | |
| $M_{300}$, MPa | 9.1 | 8.6 | 8.9 | 8.8 | 7.9 |
| UTS, MPa | 26.6 | 24.7 | 26.4 | 26.4 | 23.1 |
| Elong., % | 580 | 580 | 600 | 570 | 570 |

The data of Table 1 show that 0.4 parts of inhibitor per 100 parts by weight of rubber increase the scorch delay from 52 to 89 percent. The data further indicate that 1,3-di(t-butylthio)imidazolidinetrione is about twice as active as 1,3-di(t-octylthio)imidazolidinetrione.

Table 2 illustrates that 1-alkyl-3-(t-butylthio)-imidazolidinetriones are especially potent inhibitors. Stocks 1 and 4 are controls. The data of stock 2 show that the alkyl substituents on the alpha carbon cannot be replaced with chlorine atoms without severely suppressing inhibitor activity. 1,3-Di(trichloromethylthio)imidazolidinetrione exhibits essentially no activity (only 8% increase in scorch delay). Stock 5 illustrates the inhibitor activity of 1-(t-butylthio)imidazolidinetrione.

The inhibitors of the invention show similar activity in vulcanizable synthetic rubber compositions but generally slightly larger quantities of inhibitor are required to obtain equivalent inhibition.

Although the invention has been illustrated by typical examples, it is not limited thereto. Changes and modifications of the examples of the invention herein chosen for purposes of disclosure can be made which do not constitute departure from the spirit and scope of the invention.

The embodiments of the invention in which an exclusive property or privilege is claimed are defined as follows:

1. A vulcanizable rubber composition comprising sulfur-vulcanizable rubber, sulfur-vulcanizing agent, organic vulcanization accelerating agent and, in an amount effective to inhibit premature vulcanization, a compound of the formula

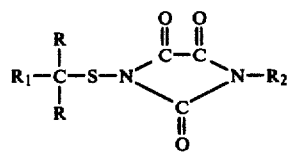

in which each R independently is alkyl of 1-5 carbon atoms, $R_1$ is alkyl of 1-12 carbon atoms, $R_2$ is hydrogen, alkyl of 1-12 carbon atoms, aryl of 6-10 carbon atoms, aralkyl of 7-10 carbon atoms or

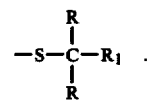

2. The composition of claim 1 in which the vulcanizing agent is elemental sulfur and the rubber is a diene rubber.

3. The composition of claim 2 in which $R_2$ is

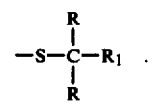

4. The composition of claim 3 in which each R is methyl.

5. The composition of claim 4 in which $R_1$ is methyl.

6. The composition of claim 2 in which $R_2$ is alkyl of 1-5 carbon atoms.

7. The composition of claim 2 in which $R_2$ is phenyl.

8. The composition of claim 7 in which each R is methyl.

9. The composition of claim 8 in which $R_1$ is methyl.

10. The composition of claim 6 in which $R_2$ is ethyl.

11. The composition of claim 10 in which each R is methyl.

12. The composition of claim 11 in which $R_1$ is methyl.

13. The composition of claim 2 in which $R_2$ is hydrogen.

14. The composition of claim 13 in which $R_1$ is alkyl of 1-5 carbon atoms.

15. The composition of claim 14 in which each R and $R_1$ are methyl.

* * * * *